United States Patent
Montalvo

(10) Patent No.: US 9,833,564 B2
(45) Date of Patent: Dec. 5, 2017

(54) FLUID CONDUIT ASSEMBLY WITH AIR VENTING FEATURES

(71) Applicant: MEDTRONIC MINIMED, INC., Northridge, CA (US)

(72) Inventor: Susan McConnell Montalvo, Woodland Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 252 days.

(21) Appl. No.: 14/553,766

(22) Filed: Nov. 25, 2014

(65) Prior Publication Data

US 2016/0144102 A1    May 26, 2016

(51) Int. Cl.
| | | |
|---|---|---|
| *A61M 5/142* | (2006.01) | |
| *A61M 5/145* | (2006.01) | |
| *A61M 5/158* | (2006.01) | |
| *A61M 5/38* | (2006.01) | |
| *A61M 39/20* | (2006.01) | |

(52) U.S. Cl.
CPC ........ *A61M 5/14244* (2013.01); *A61M 5/145* (2013.01); *A61M 5/158* (2013.01); *A61M 5/38* (2013.01); *A61M 2039/205* (2013.01); *A61M 2205/7536* (2013.01)

(58) Field of Classification Search
CPC .......... A61M 5/38; A61M 5/36; A61M 39/10; A61M 39/12; A61M 2005/1623; A61M 5/385; A61M 2205/7536; A61M 2205/7527

See application file for complete search history.

(56) References Cited

U.S. PATENT DOCUMENTS

| | | | |
|---|---|---|---|
| 3,631,847 A | 1/1972 | Hobbs, II | |
| 3,803,810 A | * 4/1974 | Rosenberg | A61M 5/38 |
| | | | 128/205.12 |

(Continued)

FOREIGN PATENT DOCUMENTS

| | | |
|---|---|---|
| DE | 4329229 | 3/1995 |
| EP | 0057001 A1 | 8/1982 |

(Continued)

OTHER PUBLICATIONS

PCT Search Report (PCT/US02/03299), dated Oct. 31, 2002, Medtronic Minimed, Inc.

(Continued)

*Primary Examiner* — Kevin C Sirmons
*Assistant Examiner* — William Carpenter
(74) *Attorney, Agent, or Firm* — Lorenz & Kopf, LLC

(57) ABSTRACT

A fluid conduit assembly for delivery of a medication fluid, and an associated fluid delivery system, are disclosed here. The fluid conduit assembly includes a trapping chamber having an interior volume to receive the medication fluid. The fluid conduit assembly also includes an inlet in fluid communication with the interior volume, a first outlet arrangement for the trapping chamber, and a second outlet arrangement for the trapping chamber. The first outlet arrangement accommodates flow of liquid from the interior volume, while inhibiting flow of gas from the interior volume. The second outlet arrangement accommodates flow of gas from the interior volume, while inhibiting flow of liquid from the interior volume.

4 Claims, 6 Drawing Sheets

(56) References Cited

U.S. PATENT DOCUMENTS

| | | | |
|---|---|---|---|
| 4,009,715 A * | 3/1977 | Forberg | A61M 5/158 210/455 |
| 4,190,426 A * | 2/1980 | Ruschke | A61M 5/36 128/205.12 |
| 4,200,095 A * | 4/1980 | Reti | A61M 5/14 604/126 |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,642,098 A * | 2/1987 | Lundquist | A61M 5/165 128/DIG. 12 |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,362,406 A * | 11/1994 | Gsell | A61M 1/3633 210/436 |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,439,587 A * | 8/1995 | Stankowski | A61M 5/165 210/321.64 |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,522,769 A | 6/1996 | DeGuiseppi | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,575,279 A * | 11/1996 | Beplate | A61M 16/0048 128/202.28 |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |

(56) References Cited

U.S. PATENT DOCUMENTS

| | | |
|---|---|---|
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,585,695 B1 * | 7/2003 | Adair ............... A61M 5/14244 604/183 |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0077598 A1 | 6/2002 | Yap et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2012/0172800 A1 | 7/2012 | Dudar et al. |
| 2013/0103002 A1 * | 4/2013 | Fruenlund ............ A61M 39/10 604/533 |

FOREIGN PATENT DOCUMENTS

| | | | |
|---|---|---|---|
| EP | 0319268 | 11/1988 | |
| EP | 0806738 | 11/1997 | |
| EP | 0880936 | 12/1998 | |
| EP | 1338295 | 8/2003 | |
| EP | 1442761 A2 | 8/2004 | |
| EP | 1631036 A2 | 3/2006 | |
| EP | 2500051 A1 | 9/2012 | |
| GB | 1401382 A | 7/1975 | |
| GB | 2218831 | 11/1989 | |
| WO | WO 95/06506 A1 | 3/1995 | |
| WO | WO 9506506 A1 * | 3/1995 | ............ A61M 5/38 |
| WO | WO 96/20745 | 7/1996 | |
| WO | WO 96/36389 | 11/1996 | |
| WO | WO 96/37246 A1 | 11/1996 | |
| WO | WO 97/21456 | 6/1997 | |
| WO | WO 98/20439 | 5/1998 | |
| WO | WO 98/24358 | 6/1998 | |
| WO | WO 98/42407 | 10/1998 | |
| WO | WO 98/49659 | 11/1998 | |
| WO | WO 98/59487 | 12/1998 | |
| WO | WO 99/08183 | 2/1999 | |
| WO | WO 99/10801 | 3/1999 | |
| WO | WO 99/18532 | 4/1999 | |
| WO | WO 99/22236 | 5/1999 | |
| WO | WO 00/10628 | 3/2000 | |
| WO | WO 00/19887 | 4/2000 | |
| WO | WO 00/48112 | 8/2000 | |
| WO | WO 02/058537 A2 | 8/2002 | |
| WO | WO 03/001329 | 1/2003 | |
| WO | WO 03/094090 | 11/2003 | |
| WO | WO 2005/065538 A2 | 7/2005 | |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

(56) References Cited

OTHER PUBLICATIONS

Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

(56) References Cited

OTHER PUBLICATIONS

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

FLUID CONDUIT ASSEMBLY WITH AIR VENTING FEATURES

TECHNICAL FIELD

Embodiments of the subject matter described herein relate generally to fluid infusion devices for delivering a medication fluid to the body of a user. More particularly, embodiments of the subject matter relate to the use of a trapping chamber in the medication fluid flow path.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., continuous insulin infusion devices such as insulin pumps) to deliver controlled amounts of insulin or other drugs to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion fluid to the body. Alternatively, the hollow tubing may be connected directly to the patient's body through a cannula or set of microneedles.

It is desirable to reduce the amount of air bubbles in a medication fluid before delivering the fluid to the patient. Small bubbles may be introduced into the medication fluid during a reservoir filling operation, for example, when the fluid reservoir is filled from a vial using a syringe. Bubbles can also be generated during temperature or altitude changes. Although patients are instructed to eliminate air from a filled reservoir, some micro bubbles may remain.

Accordingly, it is desirable to have an assembly, system, or component that is designed to mitigate the effects of air bubbles within a medication fluid flow path. Furthermore, other desirable features and characteristics will become apparent from the subsequent detailed description and the appended claims, taken in conjunction with the accompanying drawings and the foregoing technical field and background.

BRIEF SUMMARY

Disclosed herein is a fluid conduit assembly for delivery of a medication fluid. An exemplary embodiment of the fluid conduit assembly includes a trapping chamber having an interior volume to receive the medication fluid. The fluid conduit assembly also includes an inlet in fluid communication with the interior volume, a first outlet arrangement for the trapping chamber, and a second outlet arrangement for the trapping chamber. The first outlet arrangement accommodates flow of liquid from the interior volume and inhibits flow of gas from the interior volume. The second outlet arrangement accommodates flow of gas from the interior volume and inhibits flow of liquid from the interior volume.

Yet another embodiment of a fluid conduit assembly presented here includes a trapping chamber having an interior volume to receive fluid, an inlet in fluid communication with the interior volume, a delivery hole formed in a wall of the trapping chamber, a first membrane covering the delivery hole, a vent hole, and a second membrane covering the vent hole. The first membrane has hydrophilic properties to accommodate flow of liquid from the interior volume through the delivery hole while inhibiting flow of gas from the interior volume through the delivery hole. The second membrane has hydrophobic properties to accommodate flow of gas from the interior volume through the vent hole while inhibiting flow of liquid from the interior volume through the vent hole.

Another embodiment of a fluid delivery system is also presented here. The system includes a fluid infusion pump and a fluid conduit assembly coupled to the fluid infusion pump. The fluid conduit assembly includes a trapping chamber having an interior volume to receive fluid from a fluid source, a liquid outlet arrangement, and a gas outlet arrangement. The liquid outlet arrangement allows liquid to flow from the interior volume to a fluid delivery conduit while inhibiting flow of gas from the interior volume to the fluid delivery conduit. The gas outlet arrangement allows gas to exit the interior volume while inhibiting flow of liquid from the interior volume.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to certain assemblies, components, and features of a fluid infusion system of the type used to treat a medical condition of a patient. The fluid infusion system is used for infusing a medication fluid into the body of a user. The non-limiting examples described below relate to a medical device used to treat diabetes (more specifically, an insulin pump), although embodiments of the disclosed subject matter are not so limited. Accordingly, the medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. Moreover, the gas trapping filter described below could be utilized in the context of other fluid delivery systems if so desired.

For the sake of brevity, conventional features and technologies related to infusion system operation, insulin pump and/or infusion set operation, and other functional aspects of the fluid infusion system (and the individual operating components of the system) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

Figure 1:
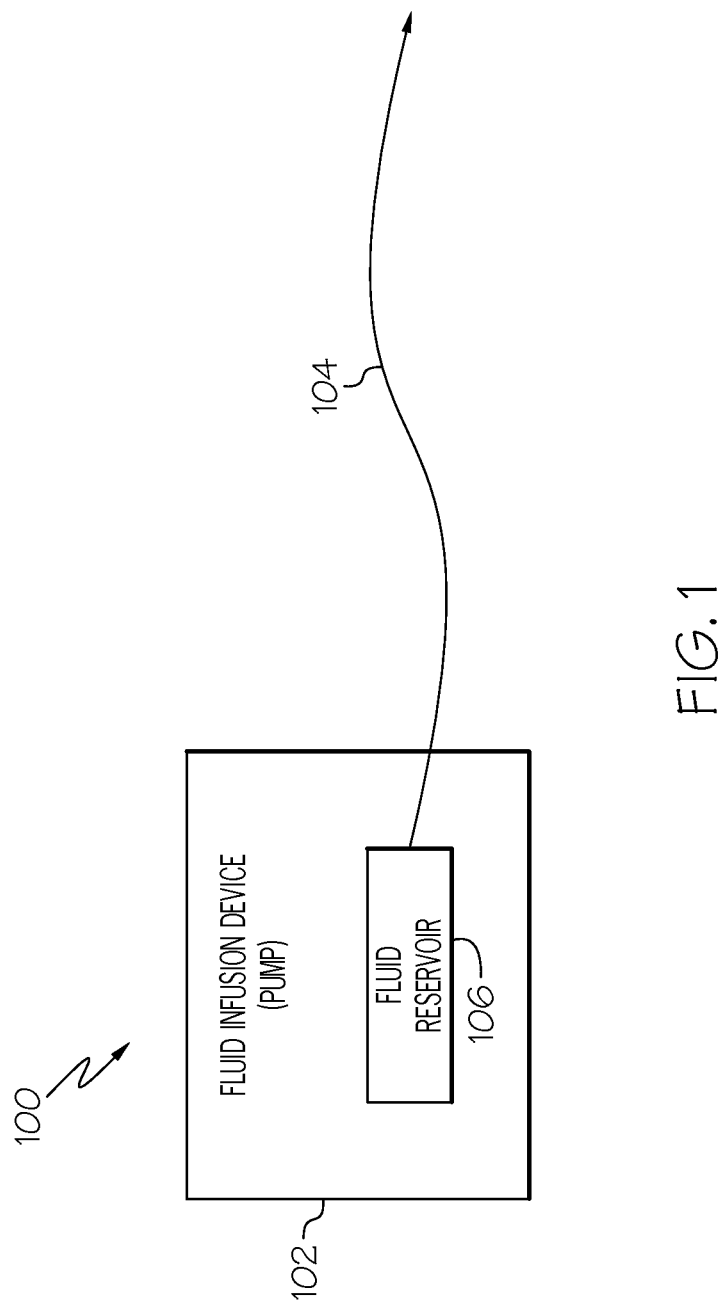
FIG. 1 is a simplified block diagram representation of an embodiment of a fluid delivery system.

FIG. 1 is a simplified block diagram representation of an embodiment of a fluid delivery system 100, which can be utilized to administer a medication fluid such as insulin to a patient. The fluid delivery system 100 includes a fluid infusion device 102 (e.g., an infusion pump) and a fluid conduit assembly 104 that is coupled to, integrated with, or otherwise associated with the fluid infusion device 102. The fluid infusion device 102 includes a fluid reservoir 106 or an equivalent supply of the medication fluid to be administered. The fluid infusion device 102 is operated in a controlled manner to deliver the medication fluid to the user via the fluid conduit assembly 104. Although not depicted in FIG. 1, the fluid conduit assembly 104 and/or the fluid reservoir 106 can be provided with a trapping chamber that receives the medication fluid and allows the liquid component of the medication fluid to flow downstream while venting gas/air that may be present in the medication fluid. In such embodiments, the trapping chamber can incorporate a gas trapping filter or membrane to inhibit downstream flow of gas/air.

Figure 2:
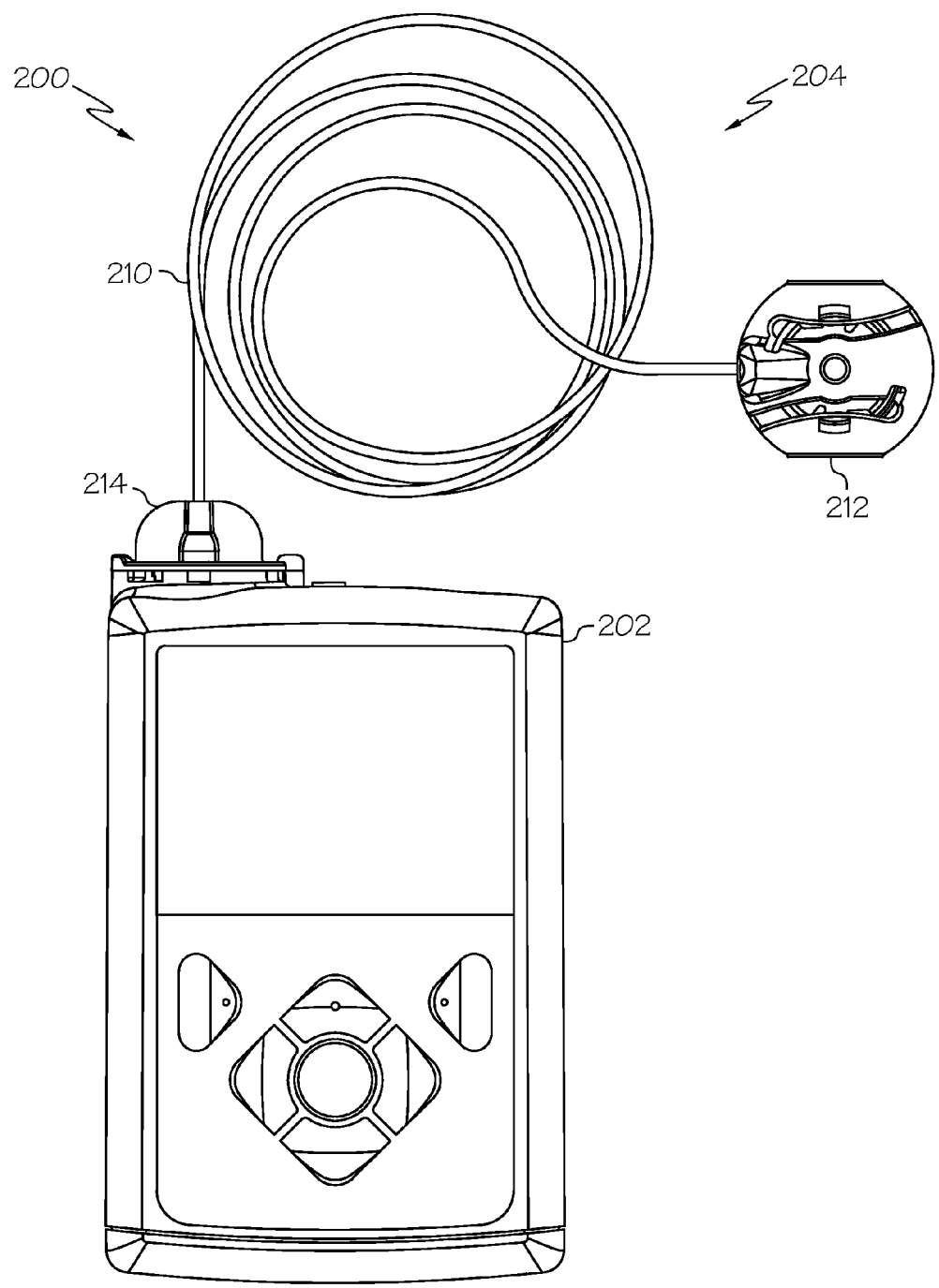
FIG. 2 is a plan view of an exemplary embodiment of a fluid delivery system that includes a fluid infusion device and an infusion set.

The fluid infusion device 102 may be provided in any desired configuration or platform. In accordance with one non-limiting embodiment, the fluid infusion device is realized as a portable unit that can be carried or worn by the patient. In this regard, FIG. 2 is a plan view of an exemplary embodiment of a fluid delivery system 200 that includes a portable fluid infusion device 202 and a fluid conduit assembly that takes the form of an infusion set component 204. For this particular embodiment, the infusion set component 204 can be coupled to the fluid infusion device 202 as depicted in FIG. 2. The fluid infusion device 202 accommodates a fluid reservoir (hidden from view in FIG. 2) for the medication fluid to be delivered to the user.

The illustrated embodiment of the infusion set component 204 includes, without limitation: a tube 210; an infusion unit 212 coupled to the distal end of the tube 210; and a connector assembly 214 coupled to the proximal end of the tube 210. The fluid infusion device 202 is designed to be carried or worn by the patient, and the infusion set component 204 terminates at the infusion unit 212 such that the fluid infusion device 202 can deliver fluid to the body of the patient via the tube 210. The fluid infusion device 202 may leverage a number of conventional features, components, elements, and characteristics of existing fluid infusion devices. For example, the fluid infusion device 202 may incorporate some of the features, components, elements, and/or characteristics described in U.S. Pat. Nos. 6,485,465 and 7,621,893, the relevant content of which is incorporated by reference herein.

The infusion set component 204 defines a fluid flow path that fluidly couples the fluid reservoir to the infusion unit 212. The connector assembly 214 mates with and couples to the neck region of the fluid reservoir, establishing the fluid path from the fluid reservoir to the tube 210. The connector assembly 214 (with the fluid reservoir coupled thereto) is coupled to the housing of the fluid infusion device 202 to seal and secure the fluid reservoir inside the housing. Thereafter, actuation of the fluid infusion device 202 causes the medication fluid to be expelled from the fluid reservoir, through the infusion set component 204, and into the body of the patient via the infusion unit 212 at the distal end of the tube 210. Accordingly, when the connector assembly 214 is installed as depicted in FIG. 2, the tube 210 extends from the fluid infusion device 202 to the infusion unit 212, which in turn provides a fluid pathway to the body of the patient. For the illustrated embodiment, the connector assembly 214 is realized as a removable reservoir cap (or fitting) that is suitably sized and configured to accommodate replacement of fluid reservoirs (which are typically disposable) as needed.

Figure 3:
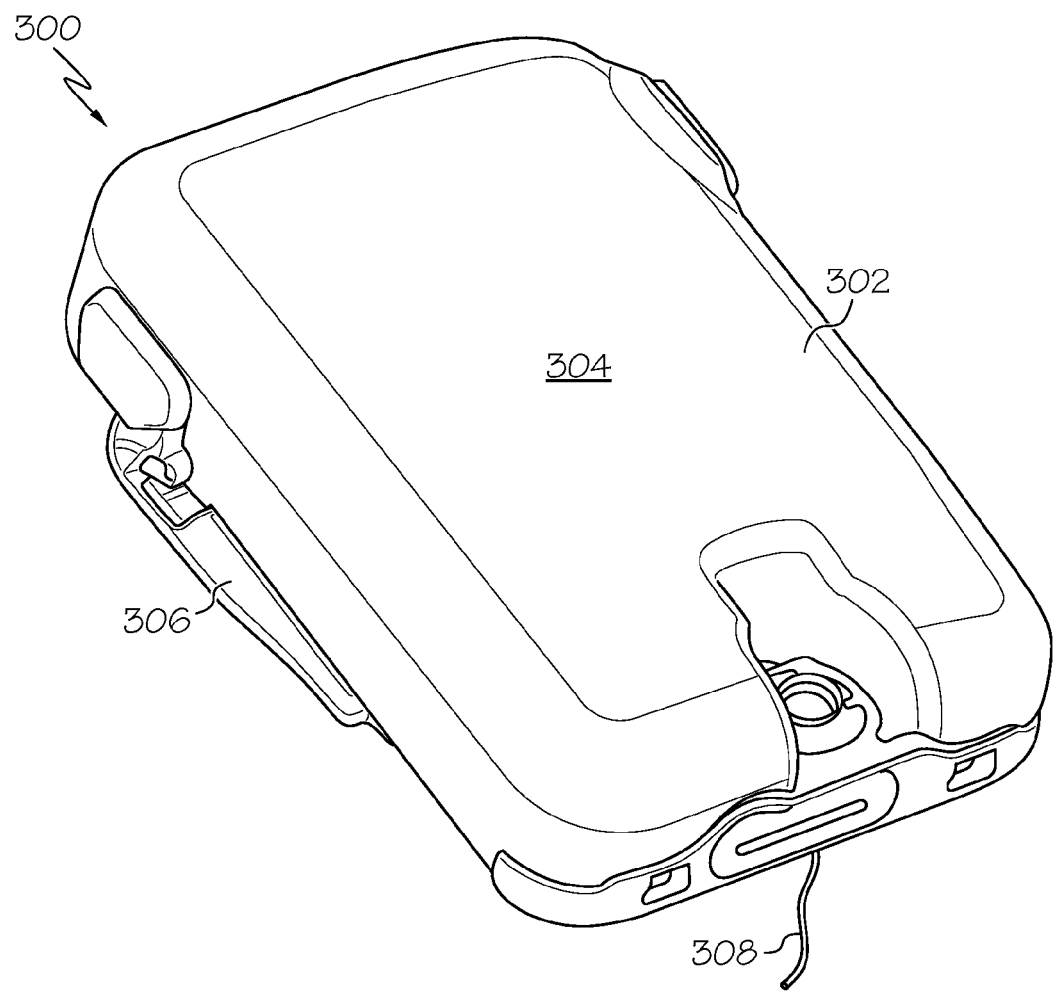
FIG. 3 is a perspective view of an exemplary embodiment of a fluid delivery system that includes a fluid infusion device designed to be affixed to the skin of the user.

FIG. 3 is a perspective view of another exemplary embodiment of a fluid delivery system 300 that includes a fluid infusion device 302 designed to be affixed to the skin of the user. The fluid infusion device 302 includes two primary components that are removably coupled to each other: a durable housing 304; and a base plate 306. The fluid infusion device 302 also includes or cooperates with a removable/replaceable fluid reservoir (which is hidden from view in FIG. 3). For this particular embodiment, the fluid reservoir mates with, and is received by, the durable housing 304. In alternate embodiments, the fluid reservoir mates with, and is received by, the base plate 306.

The base plate 306 is designed to be temporarily adhered to the skin of the patient using, for example, an adhesive layer of material. After the base plate is affixed to the skin of the patient, a suitably configured insertion device or apparatus may be used to insert a fluid delivery needle or cannula 308 into the body of the patient. The cannula 308 functions as one part of the fluid delivery flow path associated with the fluid infusion device 302. In this regard, the cannula 308 and/or other structure in fluid communication with the cannula 308 may be considered to be one implementation of the fluid conduit assembly 104 shown in FIG. 1 (or a portion thereof).

FIG. 3 depicts the durable housing 304 and the base plate 306 coupled together. For this particular embodiment, the durable housing 304 contains, among other components, a drive motor, a battery, a threaded drive shaft for the fluid reservoir, one or more integrated circuit chips and/or other electronic devices (not shown). The durable housing 304 and the base plate 306 are cooperatively configured to accommodate removable coupling of the durable housing 304 to the base plate 306. The removable nature of the durable housing 304 enables the patient to replace the fluid reservoir as needed.

Figure 4:
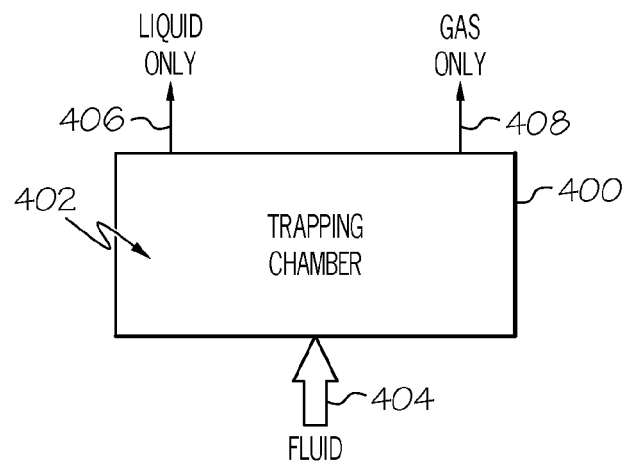
FIG. 4 is a simplified block diagram representation of an embodiment of a trapping chamber suitable for use in a fluid conduit assembly.

The fluid delivery systems 200, 300 described here are merely two exemplary embodiments that can include a fluid conduit assembly outfitted with a trapping chamber of the type described in more detail below. More specifically, the fluid delivery systems 200, 300 can manage the presence of gas/air in the medication fluid by way of a gas-venting trapping chamber, which can be incorporated into a fluid conduit assembly of the fluid delivery system. In this regard, FIG. 4 is a simplified block diagram representation of an embodiment of a trapping chamber 400 suitable for use in a fluid conduit assembly (such as the fluid conduit assembly 104, the infusion set component 204, a connector, an integrated feature of a fluid infusion device, a fluid reservoir, or the like). The trapping chamber 400 includes or defines an interior volume 402 that receives fluid, such as a medication fluid intended for delivery to the body of a patient. The trapping chamber 400 includes or cooperates with an inlet 404, which is in fluid communication with the interior volume 402. The inlet 404 may be implemented as part of the fluid conduit assembly, as part of the fluid delivery system, or the like. Fluid is provided from a fluid source (not shown), through the inlet 404, and into the interior volume 402 of the trapping chamber 400.

Ideally, medication fluid that enters the trapping chamber 400 should be free of bubbles, air, and other gas components. In practice, however, the liquid component of the medication fluid may contain some micro bubbles or trace amounts of gas. The trapping chamber 400 serves as a "staging area" for the received fluid during a fluid delivery operation. The trapping chamber 400 includes or cooperates with a liquid outlet arrangement 406 that facilitates flow of liquid out of the trapping chamber 400, and a gas outlet arrangement 408 that facilitates flow of gas out of the trapping chamber 400. More specifically, the liquid outlet arrangement 406 is suitably configured to accommodate flow of liquid from the interior volume 402 while inhibiting flow of gas from the interior volume 402. Conversely, the gas outlet arrangement 408 is suitably configured to accommodate flow of gas from the interior volume 402 while inhibiting flow of liquid from the interior volume 402. Although not depicted in FIG. 4, the gas outlet arrangement 408 can be implemented as a vent to allow gas to escape from the trapping chamber 400, and the liquid outlet arrangement 406 can be fluidly coupled to a fluid delivery conduit, a length of tubing, or the like. Thus, the liquid outlet arrangement 406 allows liquid to flow while blocking gas/air, and the gas outlet arrangement 408 allows gas to flow while blocking liquid.

The trapping chamber 400 that is schematically depicted in FIG. 4 can be implemented and realized in a variety of different ways. In some embodiments, the trapping chamber 400 is integrally formed in a reservoir cap of a fluid infusion device (see, for example, the connector assembly 214 shown in FIG. 2). In certain embodiments, the trapping chamber 400 is integrally formed in a fluid connector (such as a two-part detachable locking connector, a LUER LOK connector, or the like). In other embodiments, the trapping chamber 400 can be implemented in a fitting or a transfer guard that is utilized to transfer medication fluid (e.g., insulin) from a vial to a fluid reservoir of a fluid infusion device. Similarly, the trapping chamber 400 can be integrated into an automatic filling station that is operated to fill a fluid reservoir or an infusion device with the desired fluid. These and other implementations and embodiments are contemplated by this disclosure.

Figure 5:
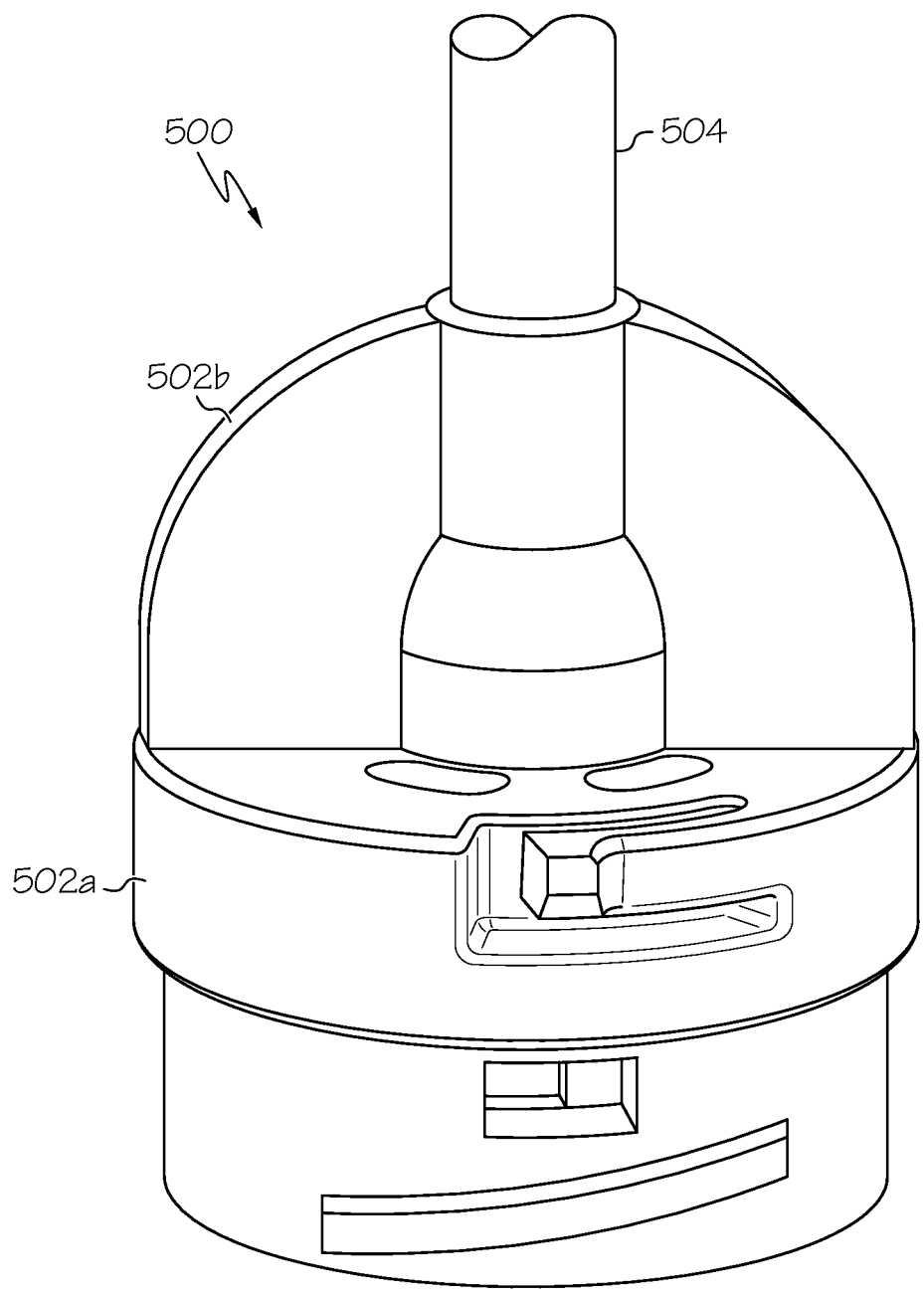
FIG. 5 is a perspective view of an embodiment of a fluid conduit assembly that is realized as a cap for a fluid reservoir.

FIG. 5 is a perspective view of a fluid conduit assembly that is realized as a connector assembly or a reservoir cap 500 for a fluid reservoir. In this regard, the reservoir cap 500 is generally configured as described above for the connector assembly 214 shown in FIG. 2. Accordingly, the reservoir cap 500 may be provided as component of a disposable infusion set.

The illustrated embodiment of the reservoir cap 500 generally includes, without limitation: a body section 502; a flow path defined in the body section; a length of tubing 504 extending from the body section 502; and a trapping chamber (hidden from view). FIG. 5 depicts the body section 502 as two sections: a lower body section 502a; and an upper body section 502b. The trapping chamber can be integrally formed in the lower body section 502a.

The lower body section 502b is suitably configured to receive a fluid reservoir, e.g., by a threaded engagement, a snap fit, tabs, or the like. The tubing 504 is physically and fluidly coupled to the upper body section 502b such that the tubing 504 is in fluid communication with the flow path. This allows the tubing 504 to carry fluid from the body section 502 during a fluid delivery operation. The flow path, much of which is hidden from view in FIG. 5, may be defined by: a hollow needle that penetrates a septum of the fluid reservoir; an internal space, chamber, or conduit of the lower body section 502a, which is upstream of the trapping chamber; and an internal space, chamber, or conduit of the upper body section 502b, which is downstream of the trapping chamber. The flow path continues into the tubing 504, which is connected to the upper body section 502b.

The trapping chamber resides within the body section 502 such that it is positioned in the flow path of the medication fluid. During a fluid delivery operation, the medication fluid is forced out of the fluid reservoir and into the hollow needle (not shown in FIG. 5). The distal end of the hollow needle terminates at a location that is upstream of the trapping chamber. This positioning ensures that the medication fluid can be provided to the trapping chamber before it exits the reservoir cap 500.

Figure 6:
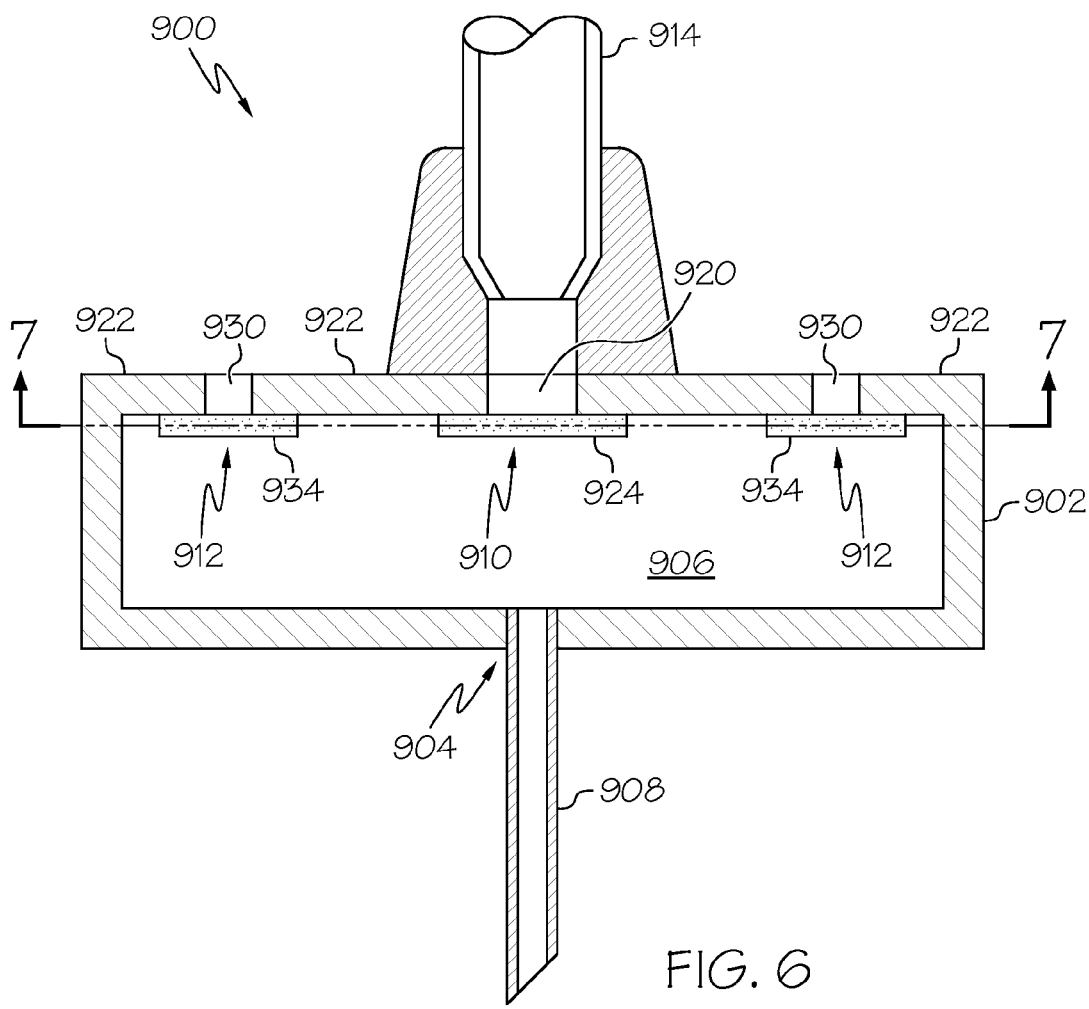
FIG. 6 is a cross-sectional view of a portion of a fluid conduit assembly having a trapping chamber.

FIG. 6 is a cross-sectional view of a portion of a fluid conduit assembly 900 having a trapping chamber 902 formed therein. This particular embodiment of the fluid conduit assembly 900 forms a part of a reservoir cap of a fluid infusion device, such as the reservoir cap 500 shown in FIG. 5. For simplicity and ease of illustration, however, surrounding structure and features of the reservoir cap are not shown or described here. Referring to FIG. 5, the trapping chamber 902 can be integrally formed in the body section 502 and in the fluid flow path. For example, the trapping chamber 902 can be located within the interior space that is generally defined by the lower body section 502a (this interior space is hidden from view in FIG. 5).

The exemplary embodiment of the fluid conduit assembly 900 generally includes, without limitation: the trapping chamber 902; an inlet 904 in fluid communication with an interior volume 906 of the trapping chamber 902; a hollow needle 908 coupled to the inlet 904; a liquid outlet arrangement 910 for the trapping chamber 902; a gas outlet arrangement 912 for the trapping chamber 902; and a length of hollow tubing 914 that serves as a fluid delivery conduit. During a fluid delivery operation, such as an insulin delivery operation of an insulin infusion pump, the desired fluid (e.g., insulin medication fluid) is dispensed from a fluid source such as a fluid reservoir. The hollow needle 908 is compatible with the fluid delivery source and the host fluid infusion system. The dispensed fluid enters the interior volume 906 by way of the hollow needle 908, which is in fluid communication with the fluid source. The liquid outlet arrangement 910 allows liquid to flow from the interior volume 906 to the hollow tubing 914, while inhibiting or preventing the flow of gas from the interior volume 906 to the hollow tubing 914. The gas outlet arrangement 912 allows gas to exit the interior volume 906, while inhibiting or preventing the flow of liquid from the interior volume 906.

The illustrated embodiment of the liquid outlet arrangement 910 includes, without limitation: at least one delivery hole 920 formed in a wall 922 of the trapping chamber 902; and at least one membrane 924 (also referred to here as the first membrane 924) covering or blocking at least a portion of the at least one delivery hole 920. For simplicity, FIG. 6 depicts only one delivery hole 920, which is formed in an upper wall 922 of the trapping chamber 902. In certain embodiments, the first membrane 924 completely covers or blocks the at least one delivery hole 920, as schematically depicted in FIG. 6. In practice, the first membrane 924 can be realized as a small disc or patch of material that is affixed or otherwise incorporated into the wall 922 as needed. It should be appreciated that the first membrane 924 can be located upstream of the delivery hole 920 (as shown), located downstream of the delivery hole 920, or positioned within the space defined by the delivery hole 920. Furthermore, more than one membrane 924 can be utilized within the defined fluid flow path if redundancy is desired.

The first membrane 924 exhibits hydrophilic properties, such that liquid can easily pass through the first membrane 924. Moreover, the properties of the first membrane 924 inhibit or prevent the flow of gas through the first membrane 924. Thus, the first membrane 924 is fabricated from a material (or materials) that is partially or predominantly hydrophilic. The hydrophilic characteristic of the first membrane 924 facilitates the flow of liquid medication fluid from the interior volume 906 to the hollow tubing 914, which is in fluid communication with the liquid outlet arrangement 910.

The first membrane 924 is formed from a suitable material, composition, or element such that the medication fluid can easily pass through the first membrane during fluid delivery operations. The first membrane 924 can be formed from a hydrophilic, semi-hydrophilic, partially hydrophilic, or predominantly hydrophilic material. Although a truly hydrophilic material may be ideal, the material used for the first membrane 924 can be partially or predominantly hydrophilic while exhibiting some amount of hydrophobicity. Non-limiting examples of suitable materials for the first membrane 924 include: polyacrylate; polyurethane; nylon; cellulose acetate; polyvinyl alcohol; polyethelene foam; polyvinyl acetate; polyester fiber felt; polyester (PET); polysulfone; polyethyl sulfone; collagen; polycaprolactone; or the like. It should be appreciated that the material or materials used to fabricate the first membrane 924 can be treated to enhance the hydrophilic characteristics if so desired.

The illustrated embodiment of the gas outlet arrangement 912 includes, without limitation: at least one vent hole 930 formed in the wall 922 of the trapping chamber 902; and at least one membrane 934 (also referred to here as the second membrane 934) covering or blocking at least a portion of the at least one vent hole 930. The cross-sectional view of FIG. 6 shows only two vent holes 930, however, the illustrated embodiment actually includes four vent holes 930 (see FIG. 7). In certain embodiments, the second membrane 934 completely covers or blocks the vent holes 930, as schematically depicted in FIG. 6. In practice, the second membrane 934 can be realized as individual pieces of material or as a unitary patch of material that is shaped and sized in accordance with the configuration of the vent holes 930. As described above for the first membrane 924, the material used for the second membrane 934 can be affixed or otherwise incorporated into the wall 922 as needed. It should be appreciated that the second membrane 934 can be located upstream of the vent holes 930 (as shown), located downstream of the vent holes 930, or positioned within the space defined by the vent holes 930. Furthermore, more than one second membrane 934 can be utilized within the defined fluid flow path if so desired.

The second membrane 934 exhibits hydrophobic properties, such that gas can easily pass through the second membrane 934. Moreover, the properties of the second membrane 934 inhibit or prevent the flow of liquid through the second membrane 934. Thus, the second membrane 934 is fabricated from a material (or materials) that is partially or predominantly hydrophobic. Indeed, the second membrane 934 can be fabricated using any suitable material or composition, including, without limitation: polytetrafluoroethylene (PTFE); fluoropolymers; glass fiber; treated or coated materials; or the like. The hydrophobic characteristic of the second membrane 934 facilitates the venting of gas/air from the interior volume 906 of the trapping chamber 902. In this regard, the vent holes 930 are preferably arranged and configured to exit into external airspace surrounding the trapping chamber 902. In other words, the vent holes 930 terminate at a location that is at ambient temperature and pressure.

In certain embodiments where the trapping chamber 902 is integrated into a reservoir cap of the type utilized with an insulin infusion pump, the hollow needle 908 receives insulin during a delivery operation that advances a piston or plunger of an insulin reservoir. In such an implementation, the interior volume 906 of the trapping chamber 902 can be within the range of about 1.0 microliters to about 500 microliters, although the actual volume may fall outside of this range in some embodiments. During a typical insulin delivery operation, the pressure within the interior volume 906 of the trapping chamber 902 can be within the range of about 1.0 psi to about 30 psi, although the actual pressure may fall outside of this range in some embodiments. The fluid pressure inside the trapping chamber 902 is sufficient to force the liquid insulin through the first membrane 924, and is sufficient to vent air or other gas components through the second membrane 934 as needed.

Figure 7:
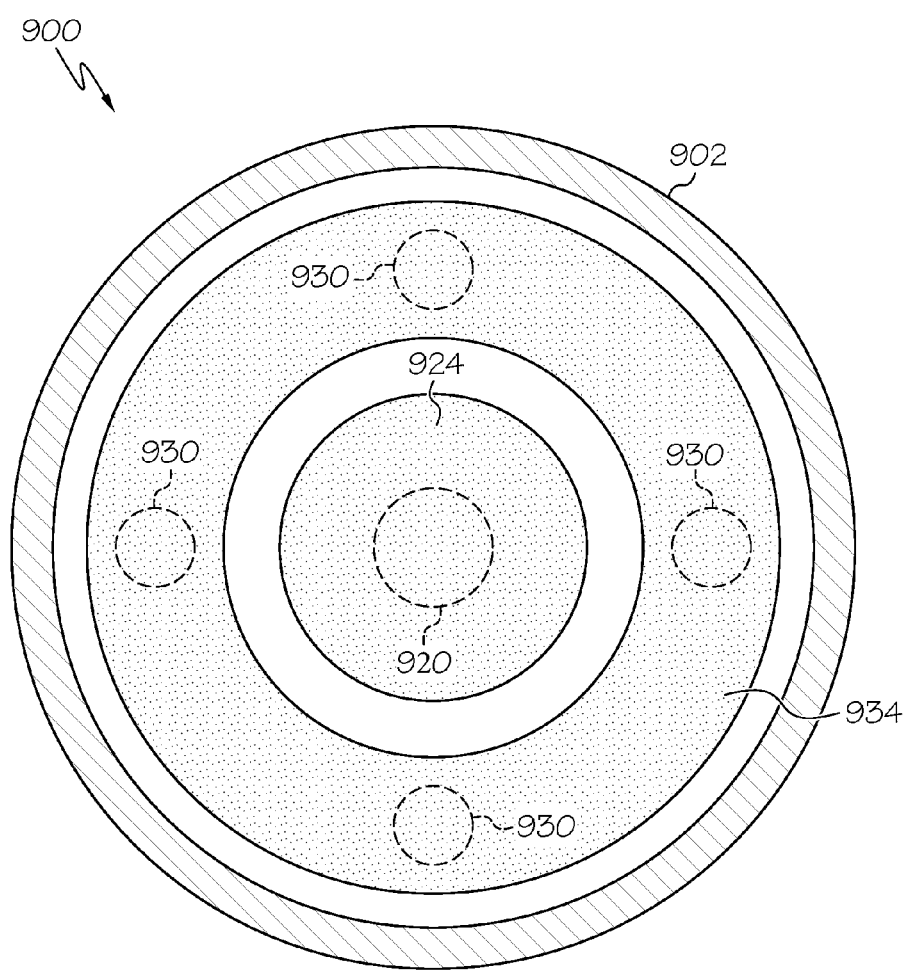
FIG. 7 is a top view of certain features of the fluid conduit assembly shown in FIG. 6.

FIG. 7 is a top view of certain features of the fluid conduit assembly 900. For ease of illustration, FIG. 7 represents some features in cross-section and some features in phantom. Moreover, the scale and proportions shown in FIG. 7 may not be consistent with that shown in FIG. 6; the features are exaggerated in FIG. 7 for clarity. The trapping chamber 902 is shown in cross-section to illustrate the arrangement and locations of the vent holes 930, the delivery hole 920, the first membrane 924, and the second membrane 934. As shown in FIG. 7, the first membrane 924 can be realized as a round disc of material that covers the delivery hole 920 without interfering with the second membrane 934 or any of the vent holes 930.

The illustrated embodiment includes four vent holes 930 formed in a circular pattern around the delivery hole 920. It should be appreciated that other venting configurations and arrangements can be utilized in lieu of that shown in FIG. 7. The circular pattern of vent holes 930 can be covered with a single ring-shaped second membrane 934. In this regard, the second membrane 934 completely covers each vent hole 930 in a way that does not interfere with the first membrane 924 or the delivery hole 920. Accordingly, air is allowed to escape from any of the vent holes 930 (via the second membrane 934), but the first membrane 924 inhibits or prevents air from traveling downstream.

As explained above, a trapping chamber can be incorporated into a reservoir cap of an infusion pump. Referring to FIG. 5 and FIG. 2, the reservoir cap receives a fluid reservoir and also seals the fluid reservoir inside the housing (the main body) of the fluid infusion device 202. More specifically, the reservoir cap seals the fluid reservoir inside a chamber or cavity of the fluid infusion device 202, and the chamber can be isolated from other sections of the fluid infusion device 202. In certain embodiments, the reservoir cap includes one or more pressure vents formed therein to equalize pressure inside the reservoir chamber of the fluid infusion device 202. Pressure equalization is desirable to ensure that the piston of the fluid reservoir does not move in response to changes in atmospheric pressure, which may be caused by altitude changes.

In addition to the trapping chamber and venting arrangement described above, a reservoir cap may also include pressure vent holes formed therein for purposes of equalizing pressure inside the reservoir chamber. In certain embodiments, the pressure vent holes are formed in the wall 922 depicted in FIG. 6, which may correspond to a top portion of the reservoir cap (see FIG. 5). In such embodiments, the pressure vent holes are external to the trapping chamber. In other words, the pressure vent holes are not in fluid communication with the interior volume of the trapping chamber. Instead, the pressure vent holes serve as a gas conduit from the volume inside the reservoir cavity that surrounds the exterior surface of the fluid reservoir.

Notably, the hydrophobic membrane 934 (see FIG. 6 and FIG. 7) that covers the vent holes 930 can be extended or otherwise configured to also cover the pressure vent holes. Accordingly, the membrane 934 facilitates equalization of air pressure inside the reservoir cavity while also inhibiting the ingress of fluid or contaminants into the reservoir cavity. Although it is preferable to use the same membrane 934 to cover the pressure vent holes and the vent holes 930, it should be understood that distinct hydrophobic membranes may be used if so desired.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid conduit assembly for delivery of a medication fluid, the fluid conduit assembly comprising:
    a reservoir cap comprising a lower body section configured to receive and couple to a fluid reservoir, and configured to couple to a housing of a fluid infusion device to seal and secure the fluid reservoir inside the housing;
    a trapping chamber integrally formed in the lower body section of the reservoir cap, the trapping chamber comprising an upper wall, a delivery hole formed in the upper wall, a plurality of vent holes formed in the upper wall and arranged around the delivery hole, and an interior volume to receive the medication fluid from the fluid reservoir;
    an inlet in fluid communication with the interior volume, the inlet formed in a lower wall of the trapping chamber, the lower wall opposing the upper wall of the trapping chamber;
    a first outlet arrangement for the trapping chamber, the first outlet arrangement accommodating flow of liquid from the interior volume and inhibiting flow of gas from the interior volume, the first outlet arrangement comprising a first membrane completely covering the delivery hole, the first membrane having hydrophilic properties;
    a length of hollow tubing in fluid communication with the first outlet arrangement by way of the delivery hole formed in the upper wall; and
    a second outlet arrangement for the trapping chamber, the second outlet arrangement accommodating flow of gas from the interior volume and inhibiting flow of liquid from the interior volume, the second outlet arrangement comprising a second membrane completely covering the plurality of vent holes, the second membrane having hydrophobic properties;
    wherein the first membrane covers the delivery hole without interfering with the second membrane and without interfering with any of the plurality of vent holes; and
    wherein the second membrane comprises a single ring-shaped membrane that surrounds the first membrane without interfering with the first membrane and without interfering with the delivery hole.

2. The fluid conduit assembly of claim 1, further comprising a hollow needle coupled to the inlet, wherein the medication fluid enters the interior volume of the trapping chamber via the hollow needle during a fluid delivery operation.

3. The fluid conduit assembly of claim 1, wherein the vent hole exits into external airspace surrounding the trapping chamber.

4. A fluid delivery system comprising:
    a fluid infusion pump; and
    a fluid conduit assembly coupled to the fluid infusion pump, the fluid conduit assembly comprising:
        a reservoir cap comprising a lower body section configured to receive and couple to a fluid reservoir, and configured to couple to a housing of the fluid infusion pump to seal and secure the fluid reservoir inside the housing;
        a trapping chamber integrally formed in the lower body section of the reservoir cap, the trapping chamber having an upper wall, a delivery hole formed in the upper wall, a plurality of vent holes formed in the upper wall and arranged around the delivery hole, and an interior volume to receive fluid from the fluid reservoir;
        an inlet in fluid communication with the interior volume, the inlet formed in a lower wall of the trapping chamber, the lower wall opposing the upper wall of the trapping chamber;

a liquid outlet arrangement that allows liquid to flow from the interior volume to a fluid delivery conduit in fluid communication with the delivery hole, while inhibiting flow of gas from the interior volume to the fluid delivery conduit, the liquid outlet arrangement comprising a first membrane completely covering the delivery hole, the first membrane having hydrophilic properties; and a gas outlet arrangement that allows gas to exit the interior volume while inhibiting flow of liquid from the interior volume, the gas outlet arrangement comprising a second membrane completely covering the plurality of vent holes, the second membrane having hydrophobic properties;

wherein the first membrane covers the delivery hole without interfering with the second membrane and without interfering with any of the plurality of vent holes; and wherein the second membrane comprises a single ring-shaped membrane that surrounds the first membrane without interfering with the first membrane and without interfering with the delivery hole.

* * * * *